(12) United States Patent
Levine

(10) Patent No.: US 10,653,366 B2
(45) Date of Patent: May 19, 2020

(54) HAPTIC FEEDBACK DEVICE, SYSTEM AND METHOD

(71) Applicant: Andrew Michael Levine, New York, NY (US)

(72) Inventor: Andrew Michael Levine, New York, NY (US)

(*) Notice: Subject to any disclaimer, the term of this patent is extended or adjusted under 35 U.S.C. 154(b) by 689 days.

(21) Appl. No.: 15/193,656

(22) Filed: Jun. 27, 2016

(65) Prior Publication Data

US 2016/0374628 A1    Dec. 29, 2016

Related U.S. Application Data

(60) Provisional application No. 62/185,143, filed on Jun. 26, 2015, provisional application No. 62/191,773, filed on Jul. 13, 2015.

(51) Int. Cl.
| | |
|---|---|
| *A61B 5/00* | (2006.01) |
| *A61F 5/56* | (2006.01) |
| *A61F 9/04* | (2006.01) |
| *A61B 5/11* | (2006.01) |

(52) U.S. Cl.
CPC .......... *A61B 5/7455* (2013.01); *A61B 5/1114* (2013.01); *A61B 5/1116* (2013.01); *A61B 5/4818* (2013.01); *A61B 5/6803* (2013.01); *A61F 5/56* (2013.01); *A61F 9/04* (2013.01); *A61B 2562/0247* (2013.01)

(58) Field of Classification Search
CPC ..... A61B 5/4818; A61B 5/486; A61B 5/6831; A61M 2021/0022; A61M 2021/0083; A61M 2209/088; A61N 1/36014
USPC .......... 128/848, 871; 600/301, 595, 544, 479
See application file for complete search history.

(56) References Cited

U.S. PATENT DOCUMENTS

| | | | |
|---|---|---|---|
| 5,381,801 A | 1/1995 | McShane et al. | |
| 8,142,373 B1* | 3/2012 | Riles | A61H 23/02 601/46 |
| 2014/0309502 A1* | 10/2014 | Levendowski | A61B 5/11 600/301 |
| 2014/0378808 A1* | 12/2014 | Lee | A61B 5/6803 600/383 |
| 2016/0296799 A1* | 10/2016 | Macagnano | A61B 5/02055 |

* cited by examiner

*Primary Examiner* — Anna K Kinsaul
*Assistant Examiner* — Caitlin A Carreiro
(74) *Attorney, Agent, or Firm* — Schmeiser, Olsen & Watts, LLP

(57) ABSTRACT

Disclosed herein is a haptic feedback device that includes a circuit board, a pressure sensor in operable communication with the circuit board, and a vibrator in operable communication with the circuit board. The vibrator is configured to vibrate when the pressure sensor senses pressure above a threshold pressure. The haptic feedback device includes a battery in operable communication with the circuit board. The circuit board, the vibrator, the pressure sensor and the battery are configured to be inserted into a wearable article such that when a wearer wears the wearable article the vibrator is configured to vibrate when the wearer is lying in the supine position. Further disclosed is a wearable sleep mask having a band for receiving the haptic feedback device, and a method of use thereof.

20 Claims, 8 Drawing Sheets

HAPTIC FEEDBACK DEVICE, SYSTEM AND METHOD

CROSS-REFERENCE TO RELATED APPLICATIONS

This application claims the benefit of U.S. Provisional Application No. 62/185,143 filed Jun. 26, 2015, and U.S. Provisional Patent Application No. 62/191,773 filed Jul. 13, 2015, each of which is incorporated herein by reference in its entirety.

FIELD OF THE TECHNOLOGY

The subject matter disclosed herein generally relates to haptic feedback. More particularly, the subject matter relates to providing sleep-positioning guidance, snoring prevention and general sleep assistance.

BACKGROUND

It has been found that sleeping on the back causes snoring and sleep apnea in some individuals. Sleeping on the back may also present a danger when an individual is in an impaired state, such as under the influence of alcohol. In these cases, sleeping on the side is optimal. However, even when a person intends to fall asleep on their side and accomplishes this goal, it is not always the case that the person remains on their side throughout the entirety of their sleep. Involuntary movement throughout the night may lead a sleeper into unwanted back-sleeping positions and may further exacerbate snoring and/or sleep apnea. Existing methodology to address these issues have been found to be complex, obtrusive and ineffective.

Therefore, a haptic feedback device, system and method configured to notify a sleeping individual that they have rolled onto their back would be well received in the art.

SUMMARY

According to one embodiment, a haptic feedback system comprises: a sleep mask adapted to be worn about the head of a wearer having a left eye covering portion and a right eye covering portion and a band extending from both the left eye covering portion and the right eye covering portion and configured to laterally extend around the head of the wearer, wherein the band includes a device receiving portion that is located at a midpoint between the left eye covering portion and the right eye covering portion in the band; and a haptic feedback device that includes: a circuit board; a pressure sensor in operable communication with the circuit board; a vibrator in operable communication with the circuit board, wherein the vibrator is configured to vibrate when the pressure sensor senses pressure above a threshold pressure; and a battery in operable communication with the circuit board; wherein the circuit board, the vibrator, the pressure sensor and the battery are located in a device receiving portion of the band.

According to another embodiment, a haptic feedback device comprises: a circuit board; a pressure sensor in operable communication with the circuit board; a vibrator in operable communication with the circuit board, wherein the vibrator is configured to vibrate when the pressure sensor senses pressure above a threshold pressure; and a battery in operable communication with the circuit board; wherein the circuit board, the vibrator, the pressure sensor and the battery are configured to be inserted into a wearable article such that when a wearer wears the wearable article the vibrator is configured to vibrate when the wearer is laying in the supine position.

According to another embodiment, a method of providing haptic feedback comprises: providing a sleep mask adapted to be worn about the head of a wearer having a left eye covering portion and a right eye covering portion and a band extending from both the left eye covering portion and the right eye covering portion and configured to laterally extend around the head of the wearer, wherein the band includes a device receiving portion that is located at a midpoint between the left eye covering portion and the right eye covering portion in the band; activating a pressure sensor located in the band as a result of a wearer of the band lying in the supine position; and vibrating a vibrator in response to the activating the pressure sensor.

BRIEF DESCRIPTION OF THE DRAWINGS

The subject matter which is regarded as the invention is particularly pointed out and distinctly claimed in the claims included at the conclusion of this specification. The foregoing and other features and advantages of the invention are apparent from the following detailed description taken in conjunction with the accompanying drawings in which:

DETAILED DESCRIPTION

A detailed description of the hereinafter-described embodiments of the disclosed apparatus and method are presented herein by way of exemplification and not limitation with reference to the Figures.

Figure 1:
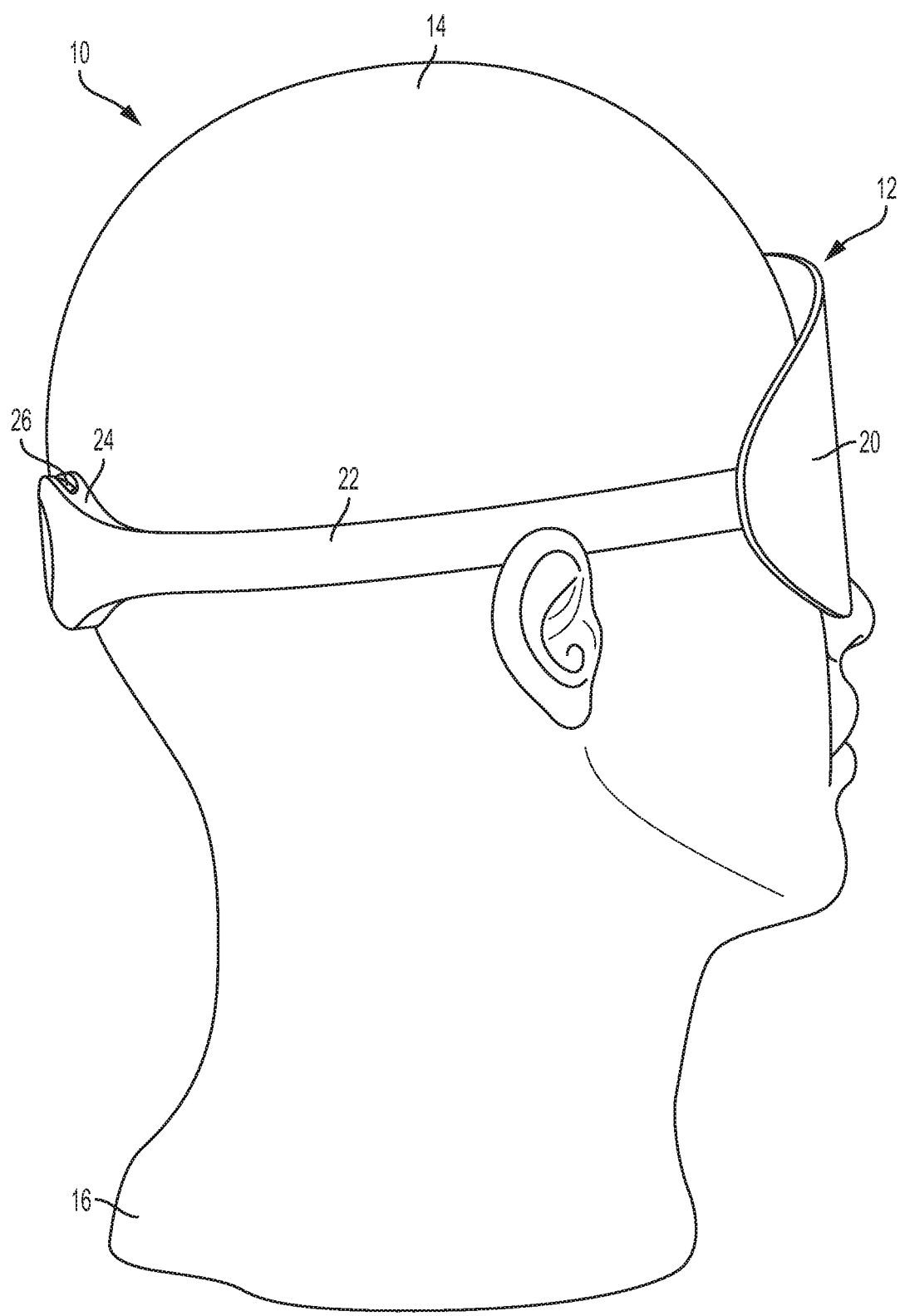
FIG. 1 depicts a perspective view of a person wearing a sleeping mask according to one embodiment.
Figure 2:
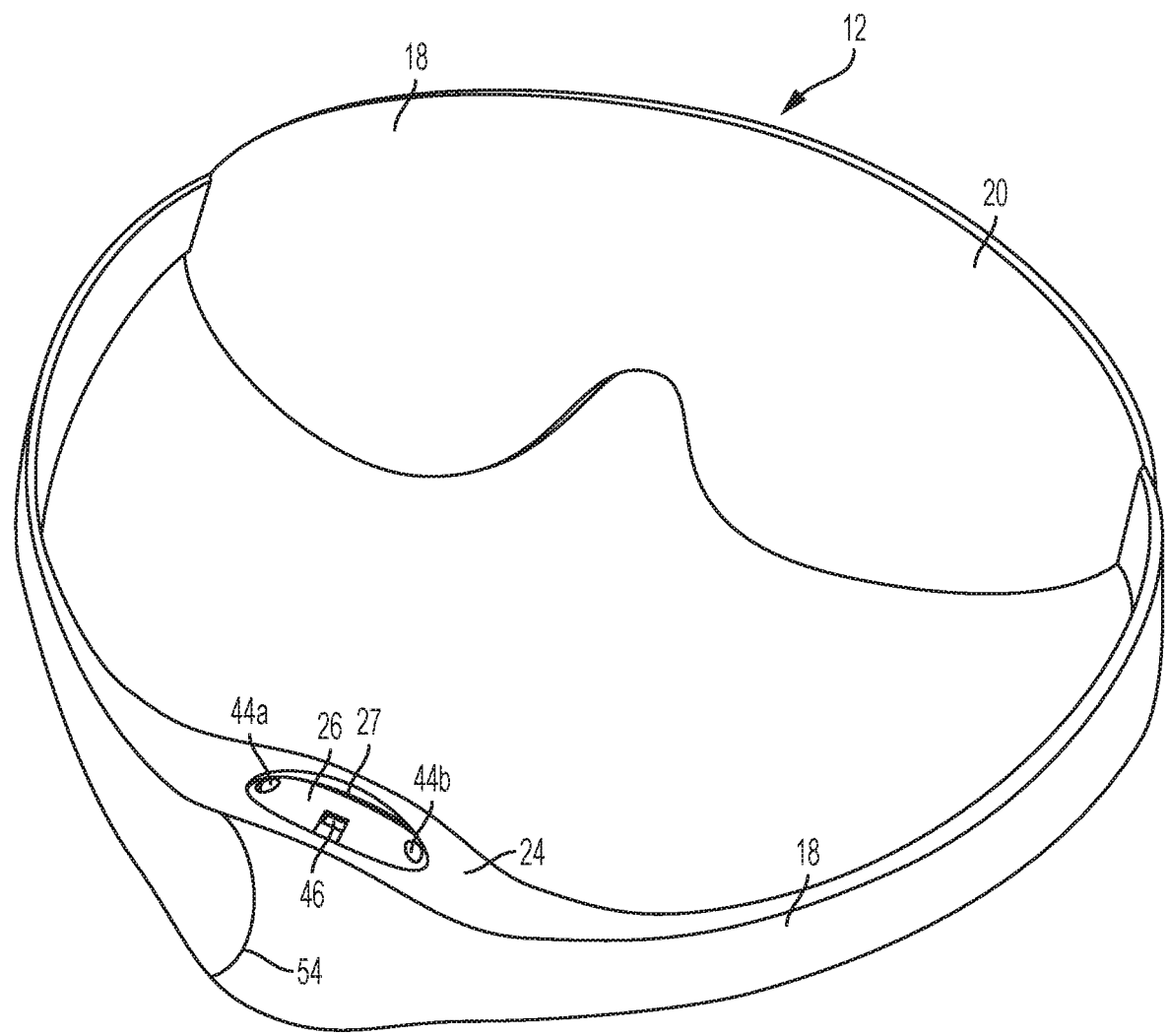
FIG. 2 depicts a perspective view of a band of the sleep mask of FIG. 1 housing a haptic feedback device according to one embodiment.
Figure 3:
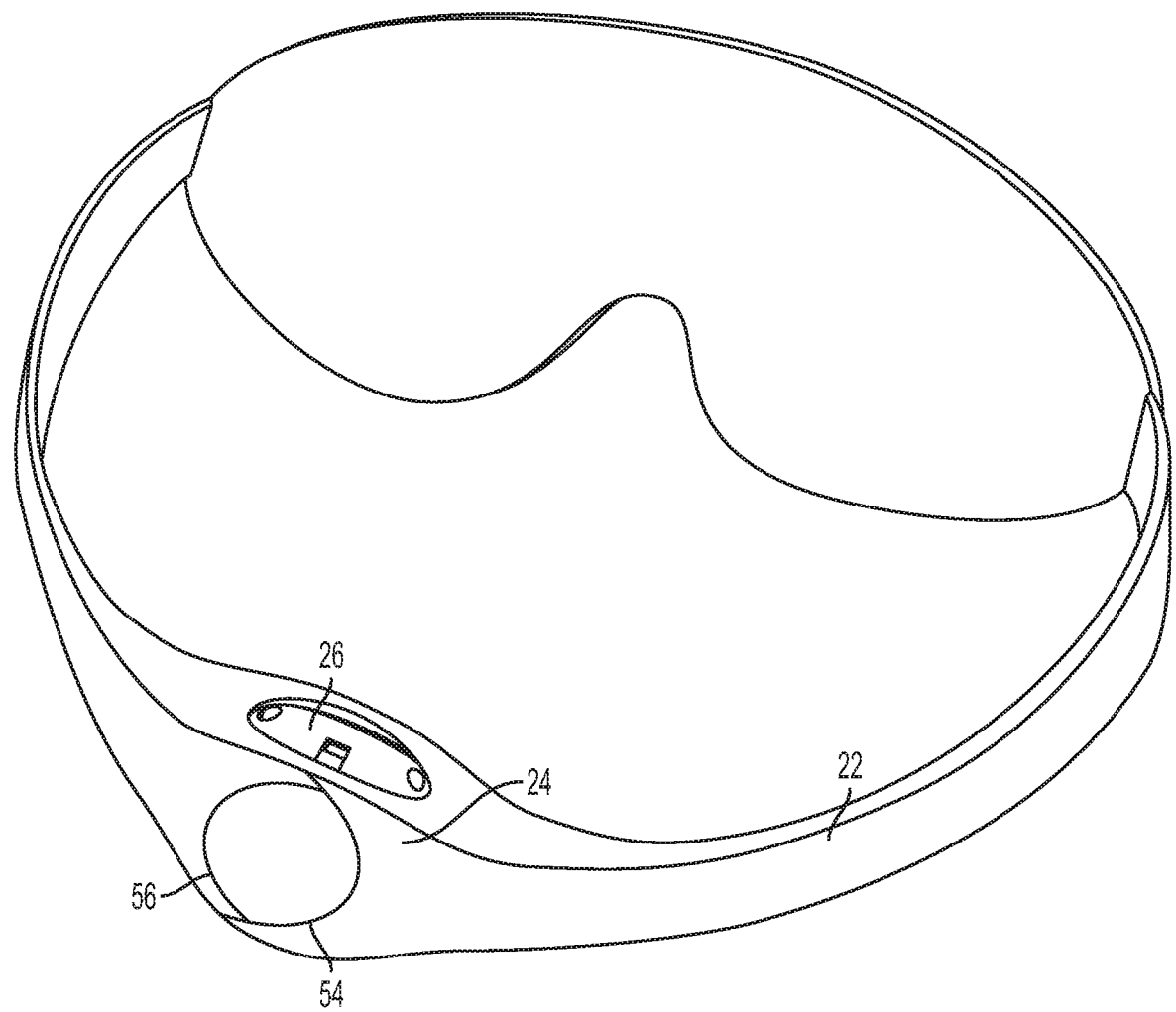
FIG. 3 depicts a perspective view of the haptic feedback device housed in the band of the sleep mask of FIG. 1-2 with a flap of the band being open according to one embodiment.
Figure 4:
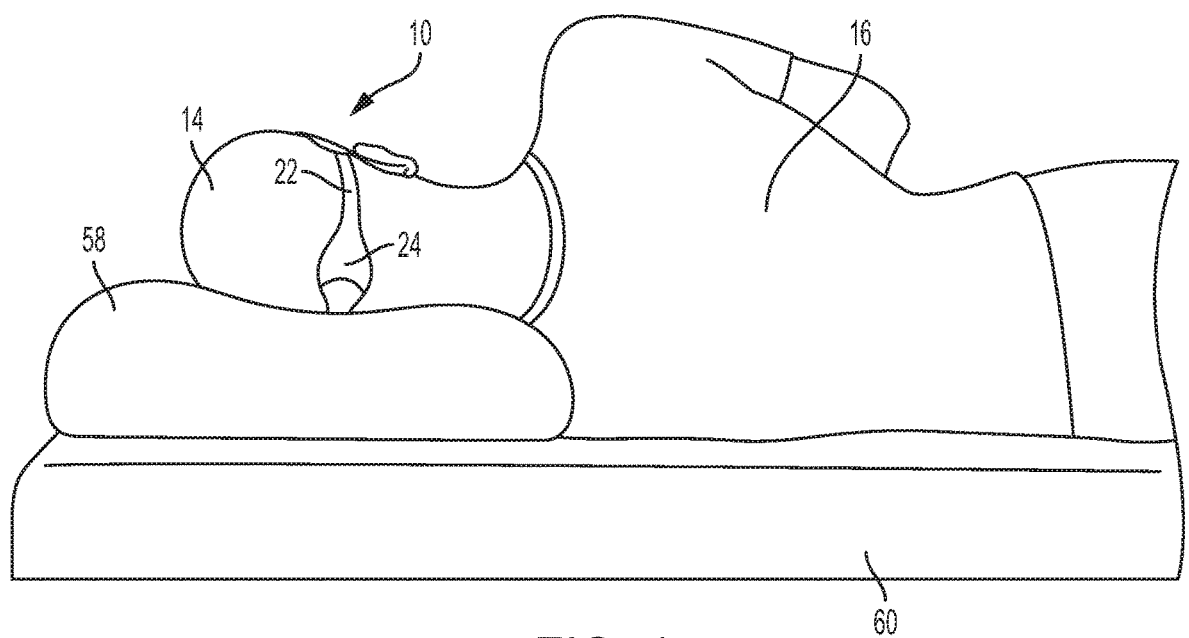
FIG. 4 depicts a side view of the person wearing the sleep mask of FIG. 1-3 resting on their side according to one embodiment.

Referring first to FIGS. 1-3, a haptic feedback system 10 is shown. The haptic feedback system 10 includes a sleep mask 12 that is adapted to be worn about the head 14 of a wearer 16. The sleep mask 12 includes a left eye covering portion 18 and a right eye covering portion 20, and a band 22 extending from both the left eye covering portion 18 and the right eye covering portion 20. The band 22 may be configured to laterally extend around the head 14 of the wearer 16, as shown. The band 22 may include a device receiving portion 24 that is located at a midpoint between the left eye covering portion 18 and the right eye covering portion 20. In other words, the haptic feedback device 26 may be centered in the middle of the band 22 so that it rests directly on the portion of the back of the head 14 that makes contact with the bed/pillow/floor or other sleeping surface while the wearer 16 is lying in the supine position. This location may be proximate, for example, at least one of the parietal and occipital region of the head 14 of the wearer 16. The device receiving portion 24 may be configured to receive a haptic feedback device 26.

Figure 6:
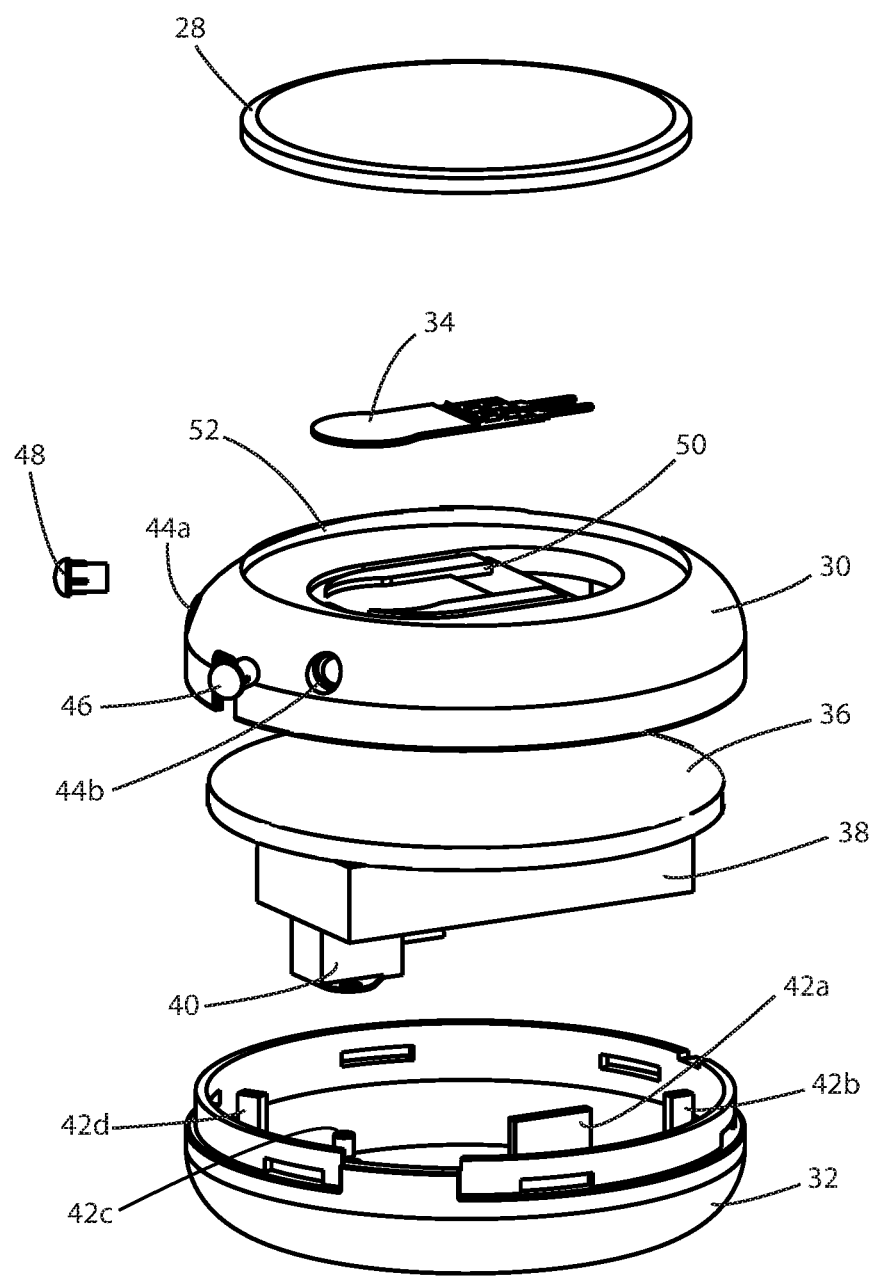
FIG. 6 depicts an exploded view of the haptic feedback device of FIGS. 1-5 according to one embodiment.

An exploded view of the haptic feedback device 26 is shown in FIG. 6. The haptic feedback device 26 may include a first outer housing 28, a second outer housing 30, a third outer housing 32, a pressure sensor 34, a circuit board 36, a battery 38, and a vibrator 40. Each of the pressure sensor 34, the vibrator 40, and the battery 38 may each be in operable communication with the circuit board 36 to provide for the herein described functionality. The circuit board 36 may be a printed circuit board or any other type of board that has a plurality of components and connecting circuits connecting the various internal components 34, 36, 38 such that they are operable in the manner described.

Figure 8:
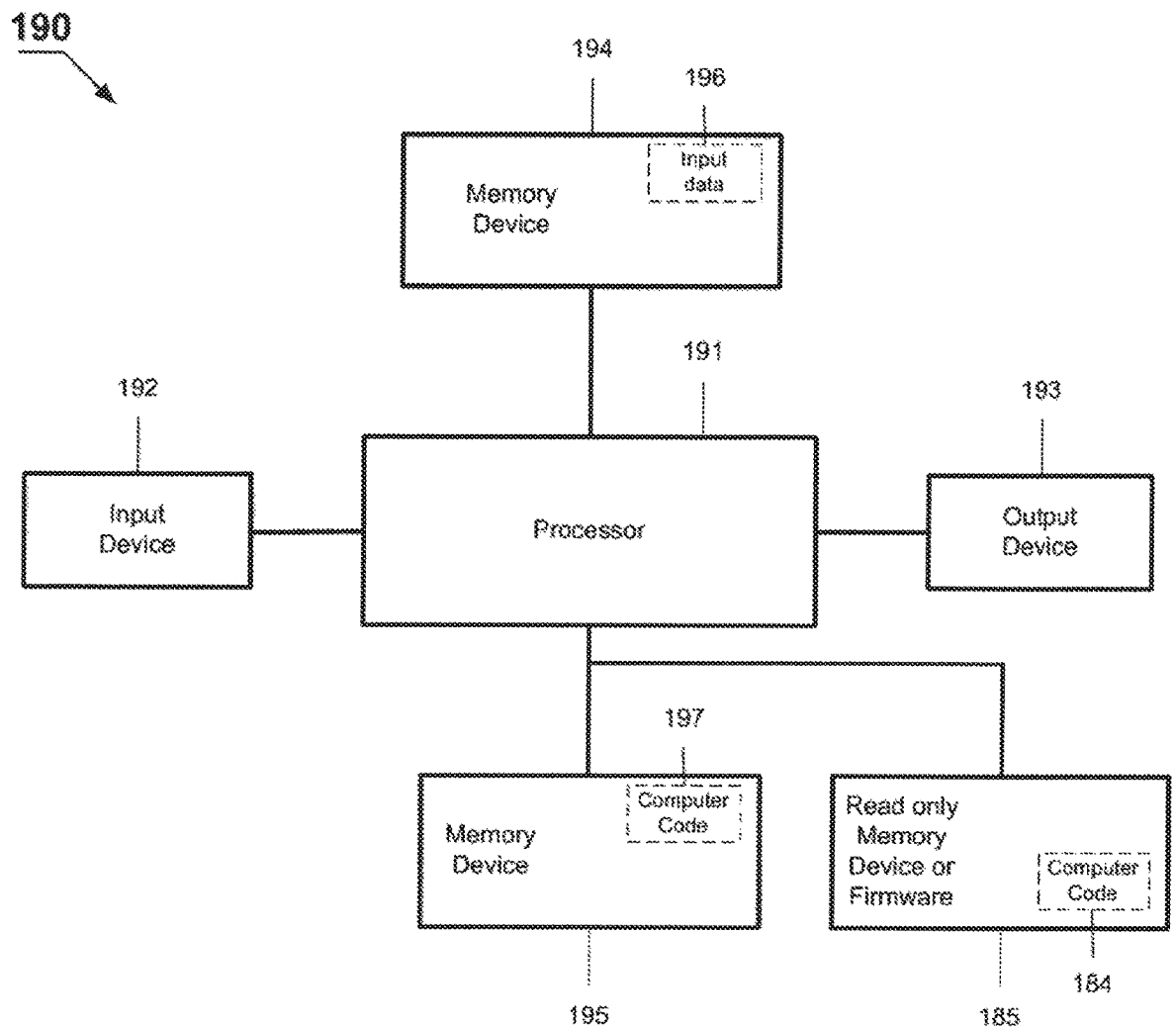

The circuit board 36 may include a processor and data storage components integrated thereon in one embodiment (as shown in FIG. 8 and described herein below). The circuit board 36 may include computer readable program instructions (e.g. machine level/low level programming) integrated as firmware into storage components found on the circuit board 36 allowing the haptic feedback device 26 to perform the functionality described. Other forms of storage and programming are contemplated, as described herein below. It should be understood that "the circuit board" hereinafter may refer to both the circuit board 36 along with the processing unit storage device integrated into or otherwise attached to the circuit board 36.

The pressure sensor 34 may be a transducer component or another type of component that is sensitive to pressure and is capable of integrating or communicating with the circuit board 36 and the vibrator 40. The circuit board 36 may be configured to receive information, signals or data from the pressure sensor 34. This data may be received and/or processed by the circuit board 36. The programmed computer readable instructions found on the circuit board 36 may be configured to cause the vibrator 40 to vibrate when the pressure sensor 34 senses pressure that is above a threshold pressure. The threshold pressure, for example, may be set higher than a pressure that is exerted on the haptic feedback device 26 by the band 22 by the device receiving portion 24. Thus, the haptic feedback device 26 can be activated by the weight of the head 14 using the pressure sensor 34. Depending on the age/weight of the individual or other factors, this trigger pressure or weight can be adjusted by controls on the haptic feedback device 26 to be more or less sensitive as described herein below. In one embodiment, the pressure sensor 34 may be set for a threshold pressure of 100 grams. In other embodiments, the pressure sensor may be set for a threshold pressure between 20 grams and 2,000 grams. Further, other threshold pressures may be used.

Figure 5:
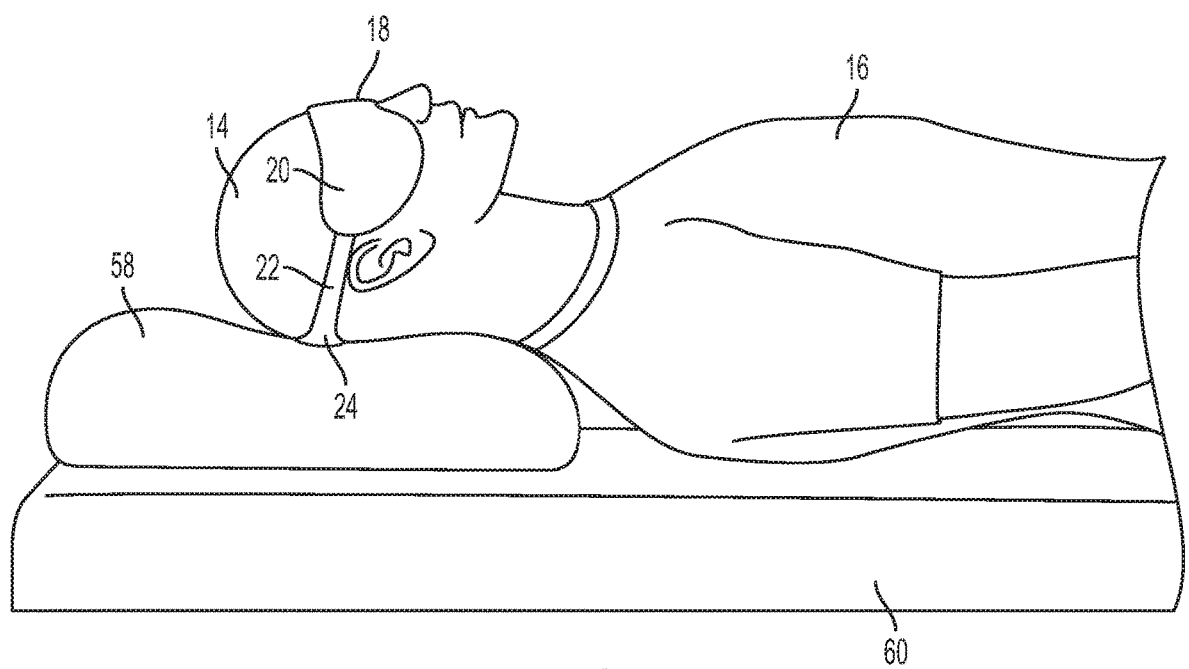
FIG. 5 depicts a side view of the person wearing the sleep mask of FIG. 1-4 resting on their back according to one embodiment.

Activation or triggering of the haptic feedback device 26 can drive the vibrator 40, which may be a built-in vibrating motor in one embodiment, to pulse vibrations, thereby inducing the wearer 16 to change sleeping position from the back to the side. The vibrator 40 may be configured to vibrate in response to the haptic feedback device 26 being triggered by, for example, being located between the wearer's head 14 and a sleeping surface 60 or pillow 58 such that the weight of the wearer's head 14 exerts a pressure on the pressure sensor 34 that exceeds the threshold pressure. Such an activated position is shown in FIG. 5. Thus, the vibrator 40 may be configured to vibrate when the wearer 16 is wearing the sleep mask 12 and lying in the supine position. However, the vibrator 40 may be configured to refrain from vibrating when the wearer 16 is wearing the sleep mask 12 and lying on their side or in another non-supine position. This functionality may be provided by computer readable program instructions found on the circuit board 36, which may be configured to receive the pressure related information from the pressure sensor 34 and output instructions to the vibrator 40 to vibrate in the above described manner. The vibrations created by the vibrator 40 may be replaced with tiny electric shocks created by the haptic feedback device 26, in one embodiment.

In one embodiment, a user interface may be provided on the haptic feedback device 26 that may, for example, include a first LED 44a, a second LED 44b, and at least one button 46. It should be understood that other forms of user interfaces are contemplated. For example, a touch screen is contemplated which includes a display. In other embodiments, additional buttons or LEDs may be provided. The user interface 44a, 44b, 46 may be in communication with the circuit board 36 and may be configured to allow for adjustment of various settings in the haptic feedback device 26 by the wearer or user.

In one embodiment, the user interface 44a, 44b, 46 may be configured to allow for adjustability in the threshold pressure. The threshold pressure may cause the pressure sensor 34 to send a signal to the circuit board 36. The pressure sensor 34 may be sensitive enough to allow for the threshold pressure to be set so that almost any change in pressure beyond any natural pressure imparted on the haptic feedback device 26 by the pocket of the device receiving portion 24, may trigger the haptic feedback device. However, this may be incrementally adjusted by the wearer 16 to prevent false positives, for example, that may be caused by a pillow or blanket touching the back of the wearer's head while the wearer is sleeping on their side. The user interface 44a, 44b, 46 may be used by the wearer 16 to reprogram a threshold pressure. Thus, the threshold pressure may be modified, adjusted, or otherwise changed by the wearer. The circuit board 36 may include computer readable program instructions that may receive and implement these adjustments in the manner described. Alternatively, the threshold pressure may be programmed into the circuit board 36 as firmware in a nonadjustable fashion.

Additionally, the user interface 44a, 44b, 46 may be configured to allow for adjustability in the intensity of the vibrator 40. For example, the vibrator 40 may have a vibration amplitude of 0.85 G in one embodiment. Other vibration amplitudes may be used. For example, an individual may not be able to detect a vibration amplitude below 0.04 G. A vibration amplitude above 1 G may be very annoying to an individual. In one embodiment, the vibrator may operate at 10,000 rpm. In other embodiments, other operating speeds may be used. The circuit board 36 may include computer readable program instructions that may receive and implement these adjustments in the manner described.

Still further, the user interface 44a, 44b, 46 may be configured to allow for adjustability in the frequency of the vibrator. For example, the vibration may be configured to vibrate every 5 seconds when the wearer 16 remains in the supine position. However, this value could be adjusted to one vibration every 3 seconds or less. Alternatively, higher frequencies are contemplated. The circuit board 36 may include computer readable program instructions that may receive and implement these adjustments in the manner described.

Even further, the user interface 44a, 44b, 46 may be configured to allow for adjustability of the length of vibration of the vibrator 40. For example, the vibration may be configured to vibrate for 0.5 seconds each time. However, this value could be adjusted to a tenth of a second or less. Alternatively, higher vibration lengths are contemplated. The circuit board 36 may include computer readable program instructions that may receive and implement these adjustments in the manner described.

The time between activation and vibration can be adjusted with the user interface 44a, 44b, 46 in order to account for any transitory movement/false positives during sleep. For example, if the wearer 16 is contacted briefly by another person who they are sleeping next to in the back of the head, a longer activation delay may preclude a vibration or activation of the haptic feedback device 26 in this situation. Thus, the circuit board 36 may require that the pressure be triggered in a constant manner for a particular set time interval before the instruction is provided to the vibrator 40 to create a vibration. The circuit board 36 may include computer readable program instructions that may receive and implement these adjustments in the manner described.

Further, in one embodiment, the vibrator 40 may be configured to stop vibrating after the wearer 16 moves out of the supine position. This may occur immediately or after a slight delay. For example, if the vibration frequency is 0.5 seconds, and the wearer 16 moves out of the supine position 0.1 second into the vibration, the vibration may still continue for another 0.4 seconds. By stopping after the wearer 16 moves out of the supine position, the haptic feedback device 26 may allow the individual to return to a restful sleep.

The haptic feedback device 26 may be programmed by the wearer 16 or other user (via the user interface 44a, 44b, 46) for a variety of different alert patterns. These may be a wide range of patterns using quick pulses, silence, and long buzzes. These patterns may be programmed to be randomized or be repetitive and may be provided by computer readable program instructions found on memory components of the circuit board 36 that may receive and implement these adjustments.

The haptic feedback device 26 may further include the outer housings 28, 30, 32 configured to house the circuit board 36, the vibrator 40, the pressure sensor 34 and the battery 38. The outer housings 28, 30, 32 may attach in a manner to create an overall outer housing that fits snugly into the device receiving portion 24 of the band 22. The first outer housing 28 may be configured to rest in a circular cavity or socket 52 in the top of the second outer housing 30 within which the first outer housing 28 may fit snugly with an interference fit. The first outer housing 28 may be in contact with the pressure sensor 34 and may be at least partially deformable such that pressure on the first outer housing 28 will be received through the first outer housing 28 by the pressure sensor 34 that is located directly underneath the first outer housing 28. The second outer housing 30 may further include another cavity or socket 50 configured to receive the pressure sensor 34 device or transducer. This second socket 50 may be directly under the first socket 52.

The second outer housing 30 may further include openings 44a, 44b, each configured to receive an LED 48. The LED's 48, once received into the openings 44a, 44b, may be in operable communication or otherwise connected to the circuit board 36. Similarly, the second outer housing 30 may include a button 46 or button opening. The button 46 may be in operable communication or otherwise connected to the circuit board 36 as well. Each of the button 46 and the LED's 48 found in the openings 44a, 44b may be exposed through an opening 27 at a top of the device receiving portion 24 of the band 22, as shown in FIG. 2. This may allow the wearer 16 to interact with the haptic feedback device 26 while it is inserted into the device receiving portion 24 of the band 22 as described hereinabove.

The outer housings, such as the outer housing 32, may further include assembly features, such as the assembly features 42a, 42b, 42c, 42d. These assembly features (such as the features 42a, 42b, 42c, 42d) may be configured to allow for the internal components such as the battery 38 and the vibrator 40 to snap or fit snugly into the outer housing portions or otherwise be assembled in a manner whereby these components do not move around within the housing 28, 30, 32 once assembled.

The outer housing combination 28, 30, 32, once assembled may be less than 3.5 cm in diameter and 1 cm in depth. Other embodiments having other dimensions are contemplated. For example, the housing combination 28, 30, 32 may be even smaller in both diameter and depth. In other embodiments, the device 10 may not be circular, but rather may include a housing of a different shape. The side of the outer housing combination 28, 30, 32 configured to be adjacent to the head 14 of the sleeper 16 may by constructed ergonomically to curve slightly for comfort and secure fit. The side of the device 10 facing the head, in the clip on use, may be coated with soft fabric for comfort. Alternatively, the bottom housing 32 (which is adjacent to the head 14 of the sleeper 16) may be made from a less rigid and softer material to provide for impressions of the bottom housing 32 by the wearer's head 14. The housing components 28, 30, 32 may be primarily made with plastic in one embodiment, although other materials are contemplated.

The device receiving portion 24 of the band 22 may be a pocket that conceals a substantial portion of the haptic feedback device 26 within the band 22. It has been found that concealing a substantial portion of the device may be desirable so that the haptic feedback system (including the mask 12, the band 22 and the device 26) is less detectable by others that are in the company of the wearer to allow the wearer to avoid possible embarrassment related to medical conditions such as snoring or sleep apnea, or other conditions.

As shown in FIG. 3, the pocket may include a first flap 54 and a second flap 56. These flaps 54, 56 may be pulled aside, as shown in FIG. 3, to provide access to the haptic feedback device 26 for reception and removal of the haptic feedback device 26 from the device receiving portion 24. In other embodiments, the haptic feedback device 26 may also be sewn directly into the fabric of the band 12 in a pouch. Still further, other mechanisms to retain the haptic feedback device 26 within the device receiving portion 24 are contemplated such as by a zipper or button or Velcro (hook and loop fastener) or a combination thereof. This may provide for removal of the haptic feedback device 26 from the band 22 in order to perform diagnostics, re-charging, or the like.

There may be a display on the haptic feedback device 26, such as the display that is provided by the LED's 44a, 44b, that displays the number of activations during a given time period or, more specifically, a night of sleep. This counter may be reset on the haptic feedback device 26 with the button 46 or other user interface. Alternatively, this counter may be reset automatically after a given time period has passed or may be reset automatically anytime the haptic feedback device 26 is charged, as described herein below.

In other embodiments, the circuit board 36 of the haptic feedback device 26 may include a wireless or wired transmitter and/or receiver and/or transceiver that may be configured to send signals to an application on a mobile device or computer (not shown). For example, the haptic feedback device 26 may include Bluetooth capabilities that allow for connection with a mobile device or other device. The mobile device or computer may keep track of the number of activations of the haptic feedback device 26. Software or application or other computer readable program instructions may be downloaded or otherwise provided on the computer or mobile device that allows the computer or mobile device to establish a connection with the haptic feedback device 26 and receive signals and other information from the haptic feedback device 26. This information may be configured to be stored by the mobile device or computer and may further be displayable when requested by a user interacting with the software or application.

The mobile device or computer may further provide for the above described functionality. In this embodiment, the circuit board 36 need not require the memory having stored the above described computer readable program instructions for implementing the functionality and adjustments described hereinabove. Instead, the mobile device or computer that is connected to the haptic feedback device 26 during use may be configured to receive the signals, data and/or information related to the pressure sensor, and may interpret these signals, data and/or information and provide instruction signals to the vibrator 40 to perform the vibrations in accordance with settings provided by the wearer. These settings may be adjusted using an interface provided by the mobile device or computer, rather than by the user interface 44a, 44b, 46 directly located on the haptic feedback device 26.

The battery 38 of the haptic feedback device 26 may provide the power necessary to provide the functionality described herein. The battery 38 may be chargeable or replaceable in nature. The haptic feedback device 26 may include the capability to charge the battery 38 with a USB cable connectable to a USB port. If the haptic feedback device 26 includes USB capabilities, the USB cable be further provide for connecting the haptic feedback device 26 to a mobile device or computer to transmit information or data.

The band 22 may be elastic one size fits all or can be adjustable fabric. The band 22 can be removable from the mask 12 in order to adjust the length without altering the center positioning of the device receiving portion 24 and the haptic feedback device 26. The band 22 may be a dual band, with two strips crisscrossing around the ears (or both above the ears) with the device receiving portion 24 centered in the back. The band 22 may take a hammock-like shape where the center of the hammock holds the device receiving portion 24 and the haptic feedback device 26 on the back of the head 14 of the wearer 16.

The band 22 may have a very thin wire running through the band 22 and/or the haptic feedback device 26 (or in contact with the haptic feedback device 26) so that vibration from the haptic feedback device 26 may be felt all around the head 14 and the ears of the wearer 16. In one embodiment, the haptic feedback device 26 may be configured to further send a signal through the wires to a pair of tiny amplifiers located in the band 22 in the ear area of the band 22. These amplifiers may be configured to emit a high frequency sound/vibration (for example, like a mosquito buzzing) which may only be heard by the individual wearing the sleep mask 12 and the haptic feedback device 26. Other types of sounds and frequencies are contemplated as well. Sounds which rouse the sleeper but not fully wake the user may be included in some embodiments. For example, in one embodiment, using the vibration amplitude of 0.85 G may be sufficient that the user will notice but may not have their sleep meaningfully disturbed. In some embodiments, the vibration from the vibrator 40 may be cushioned or lessened by other components of the haptic feedback device 26 (such as the outer housings 28, 30, 32 and other structural components) before reaching the user. Adjustment of the vibrating amplitude may be used to achieve an amplitude at which the user will notice but will not be fully awakened.

In other embodiments, the band 22 may include a plurality of device receiving portions 24 to each receive a separate haptic feedback device 26. These device receiving portions 24 may be spaced evenly along the band 22. This may help to decrease the angle at which activation occurs. For example if the sleeper 16 moves to a 45 degree angle one of the haptic feedback device's 26 may be located closer to the ear rather than directly at the back of the head. This haptic feedback device 26 may activate at this 45 degree angle as opposed to only when the wearer 16 is more closely or fully resting on their back in the supine position. This may be important in embodiments where a sleeper wants to rest fully on their side without coming close to resting on their back.

In another embodiment, the haptic feedback device 26 may include an integrated gyroscopic element to sense the angle of the person's head 14. This gyroscopic element, or accelerometer, may replace or supplement the pressure sensor 34 in some embodiments.

In one embodiment, other uses of the haptic feedback device 26 are contemplated other than snoring-prevention. For example, in one embodiment, the device may be used to prevent the wearer 16 from sleeping on their back for other reasons, such as where the wearer 16 may be under the influence of alcohol or another substance. In another embodiment, the haptic feedback device 26 may be equipped with a gyroscope/accelerometer, and may be configured to activate when the wearer's head 14 nods while driving a car, thereby preventing the wearer 16 from falling asleep at the wheel. The haptic feedback device 26 in this instance may be clipped to an eyeglass/sunglass arm or be worn similarly to the anti-back sleeping application on an eyeglasses strap (in the back/center). The haptic feedback device 26 may also be activated by pressure when the back of the wearer's head 14 pushes into the car seat. However, this functionality may be removable using the user interface 44a, 44b, 46.

Figure 7:
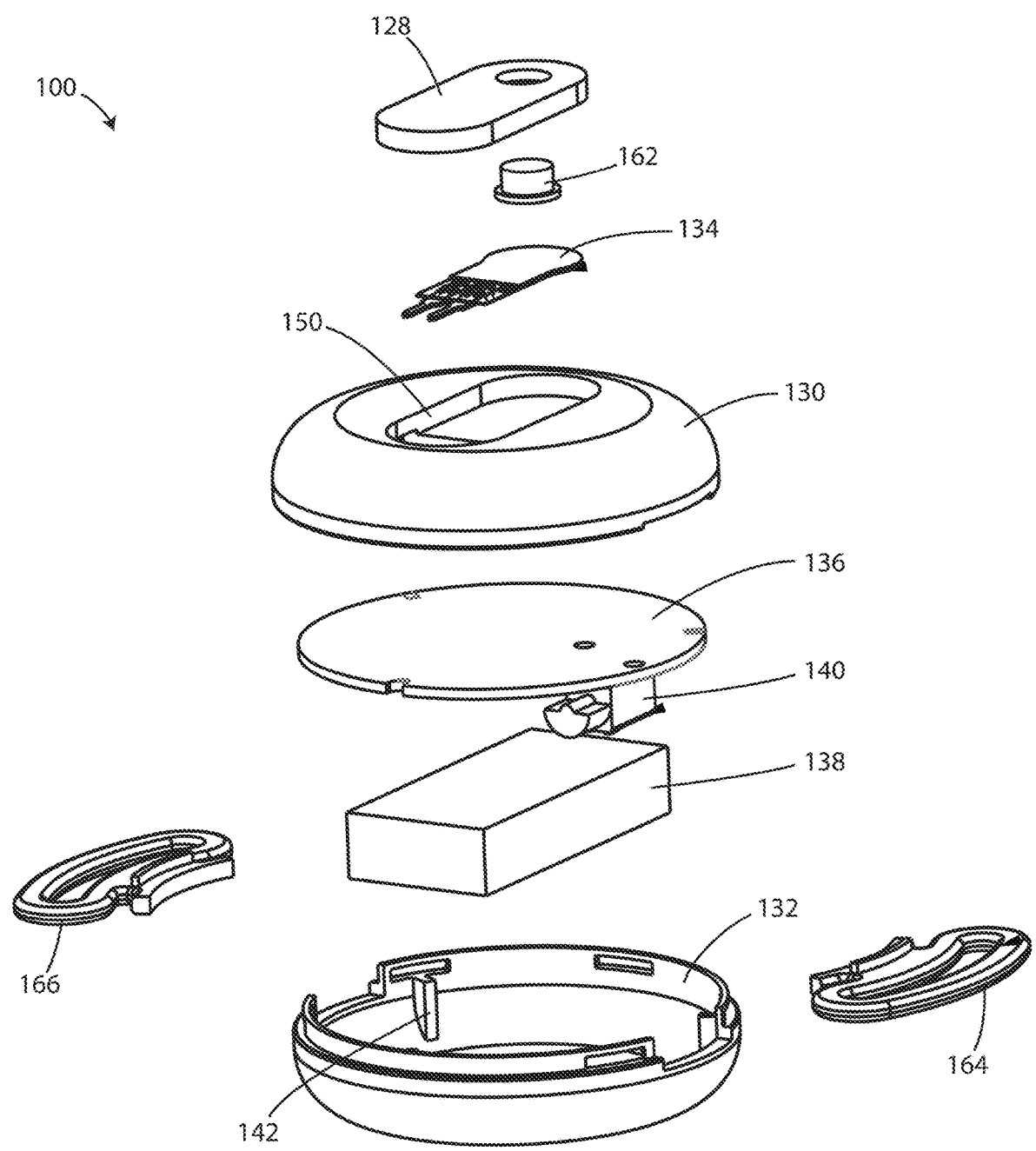
FIG. 7 depicts an exploded view of another haptic feedback device according to one embodiment.

Referring now to FIG. 7, another embodiment of a haptic feedback device 100 is shown. The haptic feedback device 100 may be similar to the haptic feedback device 26. Thus, the haptic feedback device 100 may include a battery 138, a vibrator 140, a circuit board 136, outer housing portions 128, 130, 132 having assembly features 142, and a pressure sensor 134. However, the haptic feedback device 100 may further include a button 162 and two loops 164, 166.

The button 162 may be exposed outside of the first housing portion 128 through an opening in the first housing portion 128, as shown. This button 162 may be configured to contact the transducer or pressure sensor 134, which may further be in contact or other communication with the circuit board 136. The button 162 may be found within both the first and second housing portions 128, 130, which may surround the button 162. The button 162 may extend or protrude from the first housing portion 128 and the haptic feedback device 100 in general. This may allow the button 162 to contract when the wearer 16 rolls over onto their back, thereby placing the button 162 into contact with the pressure sensor 134. This may trigger, via the circuit board 136, the vibrating element 140 to vibrate in accordance to the embodiments described hereinabove.

The device 100 in this embodiment is further shown including two plastic loops 164, 166 on opposite ends which can allow for the straps of a Velcro adjustable eye mask to be run through and attached in the middle, thereby holding the device in place against the back of the wearer's head 14. Thus, various forms of attachment to a sleep mask band are contemplated.

Haptic feedback devices in accordance with the embodiments contemplated herein may include a clipping mechanism attached to or otherwise integrated into the outer housing. Such a clipping mechanism may allow for clipping onto existing sleep masks or other devices. The clipping mechanism can be for example: 1) actuated with a latch pin on the outside of the haptic feedback device; or 2) the haptic feedback device itself may open up via a hinge and clip on to the band; or 3) the haptic feedback device may snap apart entirely and be snapped back together on the band of a sleep mask.

Alternatively a haptic feedback device consistent with the embodiments described herein may be clipped to the elastic band 12 of underpants and rest on the tailbone in another embodiment. A haptic feedback device may also be taped to the back of a bald head (with an adhesive band) or clipped to the hair in the back of the head with a latch/hair pin. Other embodiments are contemplated whereby a haptic feedback device may be placed on a back side of a sleeper such that the device may be located between the sleeper and the resting surface when a sleeper turns onto their back.

Still further, other systems are contemplated that could use a haptic feedback device such as the devices 10, 100 described herein. For example, rather than a band in a sleep mask, the haptic feedback device may be attached to a device receiving portion in a pair of pants, briefs or an undergarment around the waist at a midpoint in the back. Alternatively, the haptic feedback device may be attached to a device receiving portion in the back of a shirt, gown or the like.

Still further, methods of providing haptic feedback are contemplated. Such methods may include providing the haptic feedback system (i.e. a haptic feedback device such as the device 10, 100 and the sleep mask 12). The method may include activating a pressure sensor, such as the pressure sensor 34, located in the band, such as the band 22, as a result of a wearer of the band, such as the wearer 16, lying in the supine position. The method may include vibrating a vibrator, such as the vibrator 40, in response to the activating the pressure sensor. The method may further include adjusting the settings of the haptic feedback device in the manner described hereinabove.

Methods may further include connecting the haptic feedback device to a mobile device or a computer and sending information from the haptic feedback device to the connected mobile device or computer. Methods may include sending back instructions from the mobile device or computer to perform functionality described herein by the haptic feedback device. Methods may further include storing and displaying information, by the mobile device or computer, related to received information from the haptic feedback device. Methods may further include adjusting the settings of the haptic feedback device in the manner described herein using a mobile device or computer interface that is connected to the haptic feedback device.

It should be understood that various other methods are contemplated that perform the functionalities explicitly described hereinabove with respect to the haptic feedback devices 26, 100.

FIG. 8 illustrates a computer system 190 (e.g., the circuit board 36 and/or the entirety of the haptic feedback device 26) for enabling a methods performed by the haptic feedback device, in accordance with embodiments of the present invention.

Aspects of the present invention may take the form of an entirely hardware embodiment, an entirely software embodiment (including firmware, resident software, micro-code, etc.) or an embodiment combining software and hardware aspects that may all generally be referred to herein as a "circuit," "module," or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a solid state drive (SDD), a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing apparatus receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to methods, device (systems), and computer program products according to embodiments of the invention. It will be understood that most or all steps of the methods and functionality described herein can be implemented by computer readable program instructions.

These computer readable program instructions may be provided to a processor of a general purpose computer, special purpose computer, or other programmable data processing device (such as the haptic feedback device 26) to produce a machine, such that the instructions, which execute via the processor of the computer or other programmable data processing device, create means for implementing the functions/acts specified herein. These computer readable program instructions may also be stored in a computer readable storage medium that can direct a computer, a programmable data processing device, and/or other devices to function in a particular manner, such that the computer readable storage medium having instructions stored therein comprises an article of manufacture including instructions which implement aspects of the function/act specified herein.

The computer readable program instructions may also be loaded onto a computer, other programmable data processing device, or other device to cause a series of operational steps to be performed on the computer, other programmable device or other device (such as the haptic feedback device 26) to produce a computer implemented process, such that the instructions which execute on the computer, other programmable device, or other device implement the functions/acts specified herein.

The computer system 190 illustrated in FIG. 8 includes a processor 191, an input device 192 coupled to the processor 191, an output device 193 coupled to the processor 191, and memory devices 194 and 195 each coupled to the processor 191. The input device 192 may be, inter alia, a touchscreen, one or more push-buttons, etc. The output device 193 may be, inter alia, a computer screen, LED's, etc. The memory devices 194 and 195 may be, inter alia, a hard disk, a floppy disk, a magnetic tape, an optical storage such as a compact disc (CD) or a digital video disc (DVD), a dynamic random access memory (DRAM), a read-only memory (ROM), etc. The memory device 195 includes a computer code 197. The computer code 197 includes algorithms for enabling methods of providing haptic feedback described herein. The processor 191 executes the computer code 197. The memory device 194 includes input data 196. The input data 196 includes input required by the computer code 197. The output device 193 displays output from the computer code 197. Either or both memory devices 194 and 195 (or one or more additional memory devices such as read only memory device 196) may include the algorithms of the methods and functionality described herein and may be used as a computer usable medium (or a computer readable medium or a program storage device) having a computer readable program code embodied therein and/or having other data stored therein, wherein the computer readable program code includes the computer code 197. Generally, a computer program product (or, alternatively, an article of manufacture) of the computer system 190 may include the computer usable medium (or the program storage device).

In some embodiments, rather than being stored and accessed from a hard drive, optical disc or other writeable, rewriteable, or removable hardware memory device 195, stored computer program code 184 may be stored on a static, nonremovable, read-only storage medium such as a Read-Only Memory (ROM) device 185, or may be accessed by processor 191 directly from such a static, nonremovable, read-only medium 185. Similarly, in some embodiments, stored computer program code 184 may be stored as computer-readable firmware 185, or may be accessed by processor 191 directly from such firmware 185, rather than from a more dynamic or removable hardware data-storage device 195, such as a hard drive or optical disc.

Still yet, any of the components of the present invention could be created, integrated, hosted, maintained, deployed, managed, serviced, etc. by a service supplier who offers to enable a method of providing haptic feedback in a device such as the haptic feedback device 26. Thus the present invention discloses a process for deploying, creating, integrating, hosting, maintaining, and/or integrating computing infrastructure, including integrating computer-readable code into the computer system 190, wherein the code in combination with the computer system 190 is capable of performing a method of providing haptic feedback. In another embodiment, the invention provides a business method that performs the process steps of the invention on a subscription, advertising, and/or fee basis. That is, a service supplier, such as a Solution Integrator, could offer to enable a method of providing haptic feedback through the haptic feedback device 26. In this case, the service supplier can create, maintain, support, etc. a computer infrastructure that performs the process steps of the invention for one or more customers. In return, the service supplier can receive payment from the customer(s) under a subscription and/or fee agreement and/or the service supplier can receive payment from the sale of advertising content to one or more third parties. For example, in the embodiment where the haptic feedback device 26 is connected to a mobile device for storing data related to the haptic feedback device, the application operating on the mobile device that allows for connection and communication with the haptic feedback device 26 may be hosted by such a service supplier.

While FIG. 8 shows the computer system 190 as a particular configuration of hardware and software, any configuration of hardware and software, as would be known to a person of ordinary skill in the art, may be utilized for the purposes stated supra in conjunction with the particular computer system 190 of FIG. 8. For example, the memory devices 194 and 195 may be portions of a single memory device rather than separate memory devices.

Elements of the embodiments have been introduced with either the articles "a" or "an." The articles are intended to mean that there are one or more of the elements. The terms "including" and "having" and their derivatives are intended to be inclusive such that there may be additional elements other than the elements listed. The conjunction "or" when used with a list of at least two terms is intended to mean any term or combination of terms. The terms "first" and "second" are used to distinguish elements and are not used to denote a particular order.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

I claim:

1. A haptic feedback system comprising:
    a sleep mask adapted to be worn about the head of a wearer having a left eye covering portion and a right eye covering portion and a band extending from both the left eye covering portion and the right eye covering portion and configured to laterally extend around the head of the wearer, wherein the band includes a device receiving portion that is located at a midpoint between the left eye covering portion and the right eye covering portion in the band such that the sleep mask is configured to position the device receiving portion on the back of the wearer's head when the wearer wears the sleep mask; and
    a haptic feedback device that includes:
        a circuit board;
        a pressure sensor in operable communication with the circuit board;
        a vibrator in operable communication with the circuit board, wherein the vibrator is configured to vibrate when the pressure sensor senses pressure above a threshold pressure;
        a battery in operable communication with the circuit board;
        wherein the circuit board, the vibrator, the pressure sensor and the battery are located in the device receiving portion of the band.

2. The haptic feedback system of claim 1, wherein the vibrator is configured to vibrate when the wearer is wearing the sleep mask and lying in the supine position.

3. The haptic feedback system of claim 2, wherein the vibrator is configured to stop vibrating when the wearer moves out of the supine position.

4. The haptic feedback system of claim 1, wherein the haptic feedback device further includes an outer housing configured to house the circuit board, the vibrator, the pressure sensor and the battery, wherein the outer housing fits into the device receiving portion of the band and is securely retained by the device receiving portion of the band.

5. The haptic feedback system of claim 1, wherein the device receiving portion is a pocket that conceals a substantial portion of the haptic feedback device within the band.

6. The haptic feedback system of claim 1, wherein the vibrator is configured to vibrate in response to the haptic feedback device being located between the wearer's head and a sleeping surface such that a weight of the wearer's head exerts a pressure on the pressure sensor that exceeds the threshold pressure.

7. The haptic feedback system of claim 1, wherein the haptic feedback device includes a user interface in operable communication with the circuit board that allows for adjustability in the threshold pressure.

8. The haptic feedback system of claim 1, wherein the haptic feedback device includes a user interface in operable communication with the circuit board that allows for adjustability in an intensity of the vibrator.

9. The haptic feedback system of claim 1, wherein the haptic feedback device includes a user interface in operable communication with the circuit board that allows for adjustability in a frequency of the vibrator.

10. The haptic feedback system of claim 1, further comprising a wire in contact with the haptic feedback device, wherein the wire runs through the band, such that a vibration from the vibrator is felt throughout the band.

11. A haptic feedback device comprising:
    a circuit board;
    a pressure sensor in operable communication with the circuit board;
    a vibrator in operable communication with the circuit board, wherein the vibrator is configured to vibrate when the pressure sensor senses pressure above a threshold pressure; and
    a battery in operable communication with the circuit board;
    wherein the circuit board, the vibrator, the pressure sensor and the battery are configured to be inserted into a wearable article such that when a wearer wears the wearable article the vibrator is configured to vibrate when the wearer is laying in the supine position; and
    wherein the wearable article is configured to position the pressure sensor on the back of the wearer's head when the wearer wears the wearable article.

12. The haptic feedback device of claim 11, further comprising an outer housing configured to house the circuit board, the vibrator, the pressure sensor and the battery, wherein the outer housing fits into the wearable article and is securely retained therein.

13. The haptic feedback device of claim 11, wherein the vibrator is configured to vibrate in response to the haptic feedback device being located between the wearer's head and a sleeping surface such that a weight of the wearer's head exerts a pressure on the pressure sensor that exceeds the threshold pressure.

14. The haptic feedback device of claim 11, further comprising a user interface in operable communication with the circuit board that allows for adjustability in the threshold pressure.

15. The haptic feedback device of claim 11, wherein the haptic feedback device includes a user interface in operable communication with the circuit board that allows for adjustability of an intensity of the vibrator.

16. The haptic feedback device of claim 11, wherein the haptic feedback device includes a user interface in operable communication with the circuit board that allows for adjustability in a frequency of the vibrator.

17. The haptic feedback device of claim 11, wherein the haptic device includes a display configured to display a number of activations of the vibrator during a period of time.

18. The haptic feedback device of claim 11, further comprising a communication structure configured to communicate with at least one of a mobile device and a computer and wherein the communication structure communicates data related to activation of the vibrator to the at least one of the mobile device and the computer.

19. The haptic feedback device of claim 11, wherein the wearable article is a sleep mask including a band and wherein the circuit board, the vibrator, the pressure sensor and the battery are configured to be inserted into a band of the sleep mask.

20. The haptic feedback device of claim 11, wherein the vibrator is configured to unobtrusively vibrate such that the vibrator rouses the wearer without fully awakening the wearer.

* * * * *